United States Patent [19]

Kubota et al.

[11] Patent Number: 4,863,925
[45] Date of Patent: Sep. 5, 1989

[54] CYCLOHEXANEDIONE DERIVATIVE FOR HEPATIC DISORDERS AND A PROCESS FOR PRODUCING THE SAME

[75] Inventors: Shuhei Kubota, Upper Darby, Pa.; Kunikazu Hiraga, Osaka, Japan; Keisuke Nakayama, Ichikawa, Japan; Matazaemon Uchida, Kawachinagano, Japan

[73] Assignee: Nihon Nohyaku Co., Ltd., Tokyo, Japan

[21] Appl. No.: 99,898

[22] Filed: Sep. 22, 1987

[30] Foreign Application Priority Data

Sep. 24, 1986 [JP] Japan ................... 61-225425

[51] Int. Cl.$^4$ ................... C07D 495/04; A61K 31/50
[52] U.S. Cl. ................... 514/249; 544/350
[58] Field of Search ................... 544/350; 514/249

[56] References Cited

U.S. PATENT DOCUMENTS 4,668,799 5/1987 Yoshizawa et al. ................ 514/252

OTHER PUBLICATIONS

Chemical Abstracts, vol. 104, 1986, p. 725, Abstract No. 109609X; & JP-A-60 161 980 (Banyu Pharmaceutical Co., Ltd.) 23-08-85, Yoshizawa et al.

*Primary Examiner*—Mark L. Berch
*Attorney, Agent, or Firm*—Cushman, Darby & Cushman

[57] ABSTRACT

A cyclohexanedione derivative represented by the general formula (I);

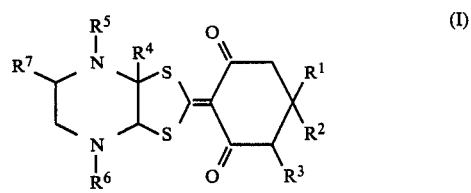

wherein $R^1$, $R^4$ and $R^7$ represent independently hydrogen atom or $C_1$–$C_8$ alkyl group, $R^2$ represents hydrogen atom; $C_1$–$C_8$ alkyl group; $C_2$–$C_6$ alkenyl group; $C_3$–$C_8$ cycloalkyl group; $C_2$–$C_7$ alkoxycarbonyl group; $C_1$–$C_6$ alkylthio $C_1$–$C_6$ alkyl group; a phenyl group; a phenyl group substituted with 1 to 3 groups selected from the group consisting of halogen atom, $C_1$–$C_6$ alkyl group, $C_1$–$C_6$ haloalkyl group, $C_1$–$C_6$ alkoxy group, $C_1$–$C_6$ alkylthio group, $C_3$–$C_8$ cycloalkoxy group, a benzyloxy group and a benzyloxy group substituted with $C_1$–$C_6$ alkoxy group; naphthyl group or a heterocyclic group, $R^3$ represents hydrogen atom, $C_1$–$C_8$ alkyl group or $C_2$–$C_7$ alkoxycarbonyl group, and $R^5$ and $R^6$, which may be the same or different, represent hydrogen atom, $C_1$–$C_6$ alkyl group, $C_2$–$C_6$ alkenyl group, $C_2$–$C_7$ alkylcarbonyl group or $C_2$–$C_7$ haloalkylcarbonyl group or its pharmaceutically acceptable salts; a pharmaceutical composition containing the same that treats hepatic disorders; and a process for producing the same.

26 Claims, No Drawings

CYCLOHEXANEDIONE DERIVATIVE FOR HEPATIC DISORDERS AND A PROCESS FOR PRODUCING THE SAME

FIELD OF THE INVENTION

This invention relates to a cyclohexanedione derivative represented by the general formula

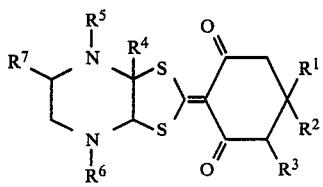

wherein $R^1$, $R^4$ and $R^{C7}$ represent independently hydrogen atom; or $C_2$-$C_8$ alkyl group, $R^2$ represents $C_1$-$C_8$ alkyl group; $C_2$-$C_{16}$ alkenyl group; $C_3$ - $C_8$ cycloalkyl group; $C_2$-$C_7$ alkoxycarbonyl group; $C_1$-$C_6$ alkylthio $C_1$-$C_6$ alkyl group; a phenyl group; a phenyl group substituted with 1 to 3 groups selected from the group consisting of halogen atom, $C_1$-$C_6$ alkyl group, $C_1$-$C_6$ haloalkyl group, $C_1$-$C_6$ alkoxy group, $C_1$-$C_6$ alkylthio group, $C_3$-$C_8$ cycloalkoxy group, a benzyloxy group and a benzyloxy group substituted with $C_1$-$C_6$ alkoxy group; naphthyl group or a heterocyclic group, $R^3$ represents hydrogen atom, $C_1$-$C_8$ alkyl group or $C_2$-$C_7$ alkoxycarbonyl group, and $R^5$ and $R^6$, which may be the same or different, represent hydrogen atom, $C_1$-$C_6$ alkyl group, $C_2$-$C_6$ alkenyl group, $C_2$-$C_7$ alkylcarbonyl group or $C_2$-$C_7$ haloalkylcarbonyl group and its pharmaceutically acceptable salts, a process for producing the same and a pharmaceutical composition containing the same.

BACKGROUND OF THE INVENTION

It has been disclosed that cyclohexanedione derivatives shown below are effective for the treatment of river damage (See U.S. Pat. No. 4,668,799)
1. 2-(1,3-dithiol-2-ylidene)-1,3-cyclohexanedione.
2. 2-(1,3-dithiol-2-ylidene)-4-methyl-1,3-cyclohexanedione.
3. 2-(1,3-dithiol-2-ylidene)-4-(2-methylethyl)-1,3-cyclohexanedione.
4. 2-(1,3-dithiol-2-ylidene)-5,5-dimethyl-1,3-cyclohexanedione.

There is still a desire, however, for a compound capable of curing and/or preventing liver disorders at a considerably lower dosage which will provide a more safety margin for treating both men and animals.

SUMMARY OF THE INVENTION

The object of the present invention is to provide a cyclohexanedione derivative represented by the aforementioned general formula (I).

The other object of the present invention is to provide a pharmaceutical composition containing as an active ingredient a compound shown by said general formula (I).

The further other object of the present invention is to provide a method for treating liver disorders in men and animals by administrating said composition to them parenterally or orally.

The further other object of the present invention is to provide a method for producing a compound represented by said general formula (I).

The terms "alkyl and alkenyl" as used herein denote both straight-chain and branched alkyl and alkenyl groups, respectively.

DETAILED DESCRIPTION OF PREFERRED EMBODIMENT

The compounds represented by the afore-mentioned general formula (I) and their salts are novel compounds not described in the literatures; they have, for example, a liver function activating effect, and hence is useful as active ingredient for a pharmaceutical composition for treating hepatic disorders in men and animals.

The compound of general formula (I) can be produced, for example, by methods A and B as shown in the following scheme:

Method A

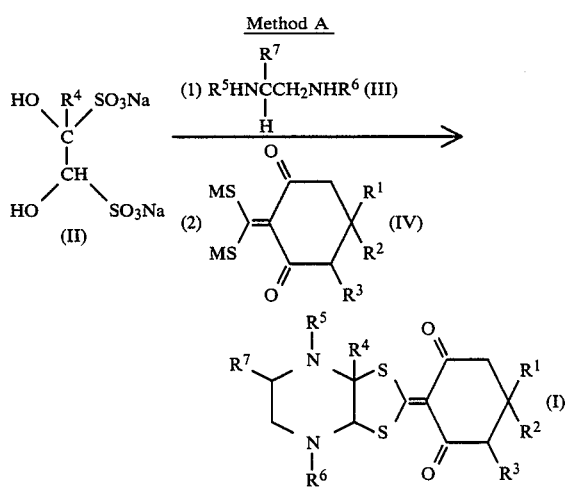

wherein $R^1$, $R^2$, $R^3$, $R^4$, $R^5$, $R^6$ and $R^7$ have the same meanings as defined above, M represents alkali metal atom.

That is, the compound of the general formula (I) can be produced by reacting the compound of the general formula (II) with the compound of the general formula (III) in a suitable solvent at a temperature in the range of from $-20°$ C. to $50°$ C. and followed by the reaction with the compound of the general formula (IV) at a temperature in the range of from $-20°$ C. to $80°$ C.

The solvents which can be used in the present reaction are preferably water or solvents consist of water and an organic solvent. For the organic solvent, there can be exemplified, for example, dimethylforamide, dimethylsulfoxide, hexamethylphosphoroamide and N,Ndimethylethyleneurea or in combination of these solvents. The reaction time depends upon the reaction temperature and reaction scale, but it may properly be selected from 1 to 24 hours. As to the molar ratio of the reagents in practicing the present reaction, they are used in equimolar amounts because the present reaction are an equimolar reaction, but either one of them may be used in excess of the other.

The compound of general formula (II) shown below can be obtained by reacting a compound of general formula (V) with an equivalent or a slightly excess of sodium bisulfite in water at temperature in the range of from $0°$ C. to $80°$ C.

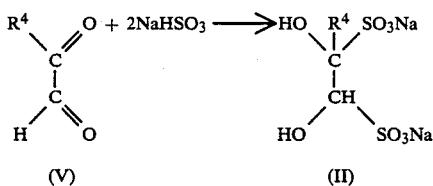

(V)  (II)

wherein $R^4$ has the same meaning as defined above. The compound of the general formula (IV) shown below can be obtained by reacting a compound of general formula (VI) with carbon disulfide in a suitable solvent in the presence of a base at a temperature in the range of from $-20°$ C. to $60°$ C.:

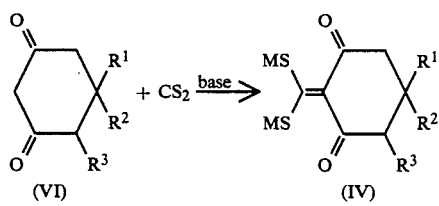

(VI)  (IV)

wherein $R^1$, $R^2$, $R^3$ and M have the same meaning as defined above.

In most case, the compound of the general formula (IV) can be used without being separated from the reaction mixture.

For a base usable in preparing the compound of the general formula (IV), there can be exemplified, for example, a hydroxide such as sodium hydroxide, potassium hydroxide and a carbonate such as sodium carbonate, potassium carbonate.

For a solvent, there can be exemplified, for example, dimethylformamide, dimethylsulfoxide, hexamethylphosphoroamide and N,N-dimethylethyleneurea etc., and in combination of these solvents or in combination of water with above organic solvents.

Method B

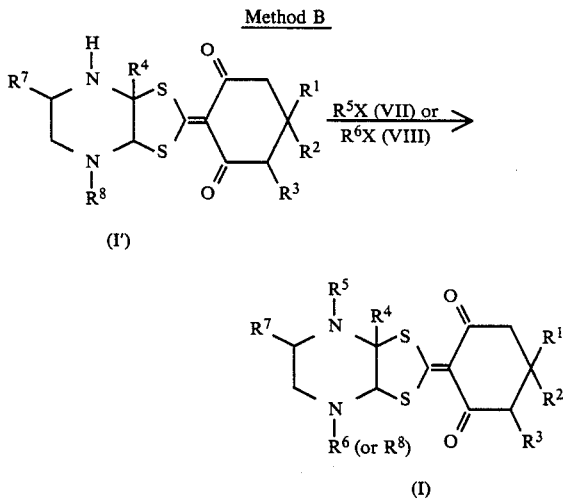

(I')

(I)

wherein $R^1$, $R^2$, $R^3$, $R^4$, $R^5$, $R^6$ and $R^7$ have the same meanings as defined above, $R^8$ represents hydrogen atom or $C_1$-$C_5$ alkyl group, and X represents halogen atom.

That is, the compound of the general formula (I) can be produced by reacting the compound of the general formula (I'), which was prepared by the method A with the compound of the general formula (VII) or (VIII) in an inert solvent at a temperature in the range of from $-20°$ C. to the boiling point of the solvent used.

Solvents which can be used in this reaction may be any of those not disturbing the reaction, and include for example ethers (e.g. diethyl ether, tetrahydrofuran, dioxane), aromatic hydrocarbons (e.g. benzene, toluene, xylene), halogenated hydrocarbons (e.g. chloroform, carbon tetrachloride). These solvents may be used alone or in combination. Bases which can be used in this reaction are inorganic bases such as sodium hydroxide, potassium hydroxide, lithium hydride, sodium hydride, etc. and organic bases such as, triethylamine, pyridine etc.

As to the amount of the base and the compound of the general formula (VII) or (VIII) used in this reaction, it suffices to use 2 mole per mole of the compound of the general formula (I') when $R^8$ represents hydrogen atom in general formula (I') and an amount equimolar to the compound of the general formula (I') when $R^8$ represents $C_1$-$C_5$ alkyl group, but amounts in excess thereof will do.

The reaction time depends upon the reaction temperature and reaction scale, but it may properly be selected from a range of 30 minutes to 8 hours.

Further, the salt of the compound of the general formula (I) was obtained by reacting the compound of the general formula (I) with the acid.

The salt of the compound of the general formula (I) may be any of pharmaceutically acceptable salt. For the acids usable in preparing the salt, there are exemplified, for example, inorganic acids such as hydrogen chloride, sulfuric acid, phosphoric acid etc., organic carboxylic acids such as acetic acid, succinic acid, fumaric acid, tartaric acid and organic sulfonic acids such as methanesulfonic acid, heptanesulfonic acid, benzenesulfonic acid, toluenesulfonic acid. For the solvents, there are exemplified, alcohol, chloroform, dichloromethane, ethyl acetate and the like.

The compound of the general formula (I) and its salt can be separated by a conventional method.

Representative examples of the compound of the general formula (I) and their salts will be shown in Table 1, but the derivatives are not limited to these examples.

Among the compound of the present invention of which the typical example are shown in Table 1 below, the preferred compounds are those whose $R^2$ represents hydrogen atom; lower ($C_1$-$C_6$) alkyl group; alkenyl group; cycloalkyl group; a phenyl group; a phenyl group substituted with 1 to 3 groups selected from the group consisting of halogen atom, lower ($C_1$-$C_6$) alkyl group, lower ($C_1$-$C_6$) haloalkoxy group, lower ($C_1$-$C_6$) alkoxy group, cycloalkoxy group, a benzyloxy group and a benzyloxy group substituted with lower ($C_1$-$C_6$) alkoxy group; naphthyl group or a heterocyclic group, and $R^5$ and $R^6$, which may be the same or different, represent hydrogen atom, lower ($C_2$-$C_6$) alkenyl group, alkylcarbonyl group or haloalkylcarbonyl group. More preferred ones are those whose $R^2$ represents hydrogen atom; $C_1$-$C_4$ alkyl group; a phenyl group; a phenyl group substituted with 1 to 2 groups selected from the group consisting of hydrogen atom, $C_1$-$C_4$ $C_4$ alkyl group and $C_1$-$C_4$ alkoxy group; or furyl group, $R^3$ represents hydrogen atom or $C_1$-$C_4$ alkyl group.

TABLE 1

| Compound No. | R¹ | R² | R³ | R⁴ | R⁵ | R⁶ | R⁷ | Physical property melting point or refractive-index |
|---|---|---|---|---|---|---|---|---|
| 1 | H | H | H | H | $CH_3$ | $CH_3$ | H | m.p. 158°–159° C. |
| 2 | H | H | H | H | $C_2H_5$ | $C_2H_5$ | H | m.p. 133° C. |
| 3 | H | H | H | H | allyl | allyl | H | m.p. 151°–153° C. |
| 4 | $CH_3$ | $CH_3$ | H | H | $CH_3$ | $CH_3$ | H | m.p. 148° C. |
| 5 | $CH_3$ | $CH_3$ | H | H | H | $CH_3$ | H | m.p. 156°–157° C. |
| 6 | $CH_3$ | $CH_3$ | H | H | $C_2H_5$ | $C_2H_5$ | H | m.p. 149°–161° C. |
| 7 | $CH_3$ | $CH_3$ | H | H | n-$C_3H_7$ | n-$C_3H_7$ | H | m.p. 121°–123° C. |
| 8 | CH | CH | H | H | allyl | allyl | H | m.p. 143°–145° C. |
| 9 | $CH_3$ | $CH_3$ | H | H | H | $C_2H_5$ | H | m.p. 145°–146° C. |
| 10 | H | H | H | H | n-$C_3H_7$ | n-$C_3H_7$ | H | m.p. 120°–122° C. |
| 11 | H | H | H | $CH_3$ | $CH_3$ | $CH_3$ | H | m.p. 155°–157° C. |
| 12 | $CH_3$ | $CH_3$ | H | $CH_3$ | $CH_3$ | $CH_3$ | H | m.p. 161°–162° C. |
| 13 | $CH_3$ | $CH_3$ | H | $CH_3$ | $C_2H_5$ | $C_2H_5$ | H | m.p. 141°–142° C. |
| 14 | $CH_3$ | $CH_3$ | H | H | H | H | $CH_3$ | m.p. 150° C. |
| 15 | $CH_3$ | $CH_3$ | H | H | $\underset{\text{CCH}_3}{\overset{\text{O}}{\|}}$ | $\underset{\text{CCH}_3}{\overset{\text{O}}{\|}}$ | $CH_3$ | m.p. 146°–150° C. |
| 16 | $CH_3$ | $CH_3$ | H | H | $CH_3$ | $\underset{\text{CCH}_3}{\overset{\text{O}}{\|}}$ | H | m.p. 171°–173° C. |
| 17 | $CH_3$ | $CH_3$ | H | H | $CH_3$ | $\underset{\text{CCF}_3}{\overset{\text{O}}{\|}}$ | H | m.p. 184°–188° C. |
| 18 | H | $CH_3$ | H | H | $CH_3$ | $CH_3$ | H | m.p. 164°–166° C. |
| 19 | H | $C_2H_5$ | H | H | $CH_3$ | $CH_3$ | H | $n_D^{17}$ 1.5880 |
| 20 | H | n-$C_3H_7$ | H | H | $CH_3$ | $CH_3$ | H | $n_D^{17}$ 1.5847 |
| 21 | H | sec-$C_4H_9$ | H | H | $CH_3$ | $CH_3$ | H | m.p. 102°–104° C. |
| 22 | H | —CH($CH_3$)$CH_2CH_2CH_3$ | H | H | $CH_3$ | $CH_3$ | H | $n_D^{17}$ 1.5769 |
| 23 | H | —$CH_2$CH($CH_3$)$CH_2CH_2$CH=C($CH_3$)$_2$ | H | H | $CH_3$ | $CH_3$ | H | $n_D^{17}$ 1.5788 |
| 24 | H | H | $CH_3$ | H | $CH_3$ | $CH_3$ | H | m.p. 148°–150° C. |
| 25 | H | H | $C_2H_5$ | H | $CH_3$ | $CH_3$ | H | m.p. 59°–60° C. |
| 26 | H | —C₆H₅ (phenyl) | H | H | $CH_3$ | $CH_3$ | H | m.p. 149°–153° C. |
| 27 | H | —C₆H₅ (phenyl) | H | H | $C_2H_5$ | $C_2H_5$ | H | m.p. 164°–165° C. |
| 28 | H | —C₆H₅ (phenyl) | H | H | n-$C_3H_7$ | n-$C_3H_7$ | H | m.p. 122°–124° C. |
| 29 | H | —C₆H₅ (phenyl) | H | H | n-$C_4H_9$ | n-$C_4H_9$ | H | m.p. 130°–132° C. |
| 30 | H | —C₆H₄-Cl (4-chlorophenyl) | H | H | $CH_3$ | $CH_3$ | H | m.p. 188°–189° C. |

TABLE 1-continued

| Compound No. | R¹ | R² | R³ | R⁴ | R⁵ | R⁶ | R⁷ | Physical property melting point or refractive-index |
|---|---|---|---|---|---|---|---|---|
| 31 | H | 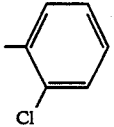 2-Cl-C₆H₄ | H | H | H | CH₃ | H | m.p. 146°–148° C. |
| 32 | H | 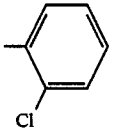 2-Cl-C₆H₄ | H | H | CH₃ | CH₃ | H | m.p. 184°–186° C. |
| 33 | H | 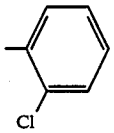 2-Cl-C₆H₄ | H | H | C₂H₅ | C₂H₅ | H | m.p. 158°–159° C. |
| 34 | H | 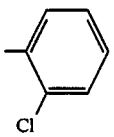 2-Cl-C₆H₄ | H | H | n-C₃H₇ | n-C₃H₇ | H | m.p. 115°–116° C. |
| 35 | H | 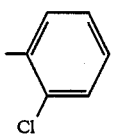 2-Cl-C₆H₄ | H | H | allyl | allyl | H | m.p 145°–146.5° C. |
| 36 | H | 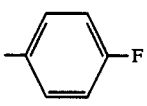 4-F-C₆H₄ | H | H | CH₃ | CH₃ | H | m.p. 176°–178° C. |
| 37 | H | 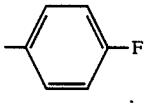 4-F-C₆H₄ | H | H | C₂H₅ | C₂H₅ | H | m.p. 84°–88° C. |
| 38 | H | 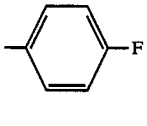 4-F-C₆H₄ | H | H | n-C₃H₇ | n-C₃H₇ | H | m.p. 103°–107° C. |
| 39 | H | 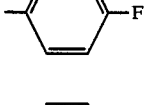 4-F-C₆H₄ | H | H | allyl | allyl | H | m.p. 139°–141° C. |
| 40 | H | 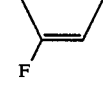 2-F-C₆H₄ | H | H | CH₃ | CH₃ | H | m.p. 161° C. |

TABLE 1-continued

| Compound No. | R¹ | R² | R³ | R⁴ | R⁵ | R⁶ | R⁷ | Physical property melting point or refractive-index |
|---|---|---|---|---|---|---|---|---|
| 41 | H | 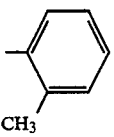 2-CH₃-phenyl | H | H | CH₃ | CH₃ | H | m.p. 162° C. |
| 42 | H | 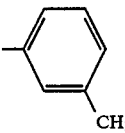 3-CH₃-phenyl | H | H | CH₃ | CH₃ | H | m.p. 111°–114° C. |
| 43 | H | 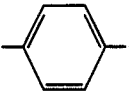 4-CH₃-phenyl | H | H | CH₃ | CH₃ | H | m.p. 156° C. |
| 44 | H | 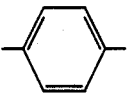 4-CH₃-phenyl | H | H | C₂H₅ | C₂H₅ | H | m.p. 224°–227° C. |
| 45 | H | 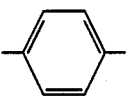 4-CH₃-phenyl | H | H | n-C₃H₇ | n-C₃H₇ | H | m.p. 141°–142° C. |
| 46 | H | 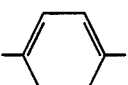 4-CH₃-phenyl | H | H | allyl | allyl | H | m.p. 132°–135° C. |
| 47 | H | 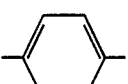 4-CH₃-phenyl | H | CH₃ | CH₃ | CH₃ | H | m.p. 107°–110° C. |
| 48 | H | 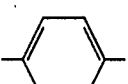 4-C₂H₅-phenyl | H | H | CH₃ | CH₃ | H | m.p. 157°–160° C. |
| 49 | H | 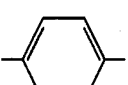 4-C₂H₅-phenyl | H | H | C₂H₅ | C₂H₅ | H | m.p. 146°–147° C. |
| 50 | H | 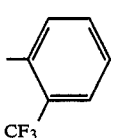 2-CF₃-phenyl | H | H | CH₃ | CH₃ | H | m.p. 89°–91° C. |
| 51 | H | 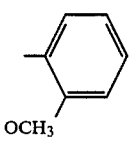 2-OCH₃-phenyl | H | H | CH₃ | CH₃ | H | m.p. 164°–165° C. |

TABLE 1-continued

| Compound No. | R¹ | R² | R³ | R⁴ | R⁵ | R⁶ | R⁷ | Physical property melting point or refractive-index |
|---|---|---|---|---|---|---|---|---|
| 52 | H | 3-OCH₃-C₆H₄- | H | H | CH₃ | CH₃ | H | m.p. 152°–153° C. |
| 53 | H | 4-OCH₃-C₆H₄- | H | H | H | H | H | m.p. 160°–162° C. |
| 54 | H | 4-OCH₃-C₆H₄- | CH₃ | H | CH₃ | CH₃ | H | m.p. 98°–101° C. |
| 55 | H | 4-OCH₃-C₆H₄- | H | H | CH₃ | CH₃ | H | m.p. 171°–172° C. |
| 56 | H | 4-OCH₃-C₆H₄- | H | H | C₂H₅ | C₂H₅ | H | m.p. 137°–140° C. |
| 57 | H | 4-OCH₃-C₆H₄- | H | H | n-C₃H₇ | n-C₃H₇ | H | m.p. 132°–34° C. |
| 58 | H | 4-OCH₃-C₆H₄- | H | H | allyl | allyl | H | m.p. 137°–139.5° C. |
| 59 | H | 4-OCH₃-C₆H₄- | H | CH₃ | CH₃ | CH₃ | H | m.p. 96°–99° C. |
| 60 | H | 4-OC₂H₅-C₆H₄- | H | H | CH₃ | CH₃ | H | m.p. 168°–170° C. |
| 61 | H | 4-OC₂H₅-C₆H₄- | H | H | C₂H₅ | C₂H₅ | H | m.p. 146°–148° C. |
| 62 | H | 4-OC₂H₅-C₆H₄- | H | H | n-C₃H₇ | n-C₃H₇ | H | m.p. 137°–140° C. |
| 63 | H | 4-OC₂H₅-C₆H₄- | H | CH₃ | CH₃ | CH₃ | H | m.p. 94°–97° C. |

TABLE 1-continued
| Compound No. | R¹ | R² | R³ | R⁴ | R⁵ | R⁶ | R⁷ | Physical property melting point or refractive-index |
|---|---|---|---|---|---|---|---|---|
| 64 | H | 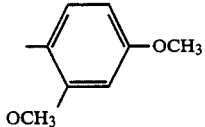 | H | H | CH₃ | CH₃ | H | m.p. 110°–113° C. |
| 65 | H | 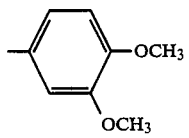 | H | H | CH₃ | CH₃ | H | m.p. 146°–148° C. |
| 66 | H | 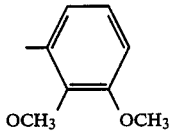 | H | H | CH₃ | CH₃ | H | m.p. 181° C. |
| 67 | H | 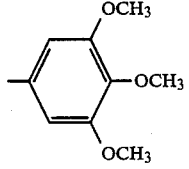 | H | H | CH₃ | CH₃ | H | m.p. 103°–106° C. |
| 68 | H | 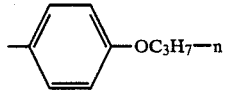 | H | H | CH₃ | CH₃ | H | m.p. 118°–121° C. |
| 69 | H | 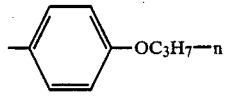 | H | H | C₂H₅ | C₂H₅ | H | m.p. 213°–214° C. |
| 70 | H | 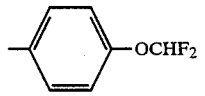 | H | H | CH₃ | CH₃ | H | m.p. 223°–225° C. |
| 71 | H | 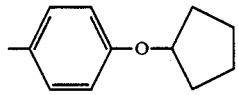 | H | H | CH₃ | CH₃ | H | m.p. 109°–113° C. |
| 72 | H | 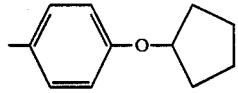 | H | H | n-C₃H₇ | n-C₃H₇ | H | m.p. 99°–101° C. |
| 73 | H | 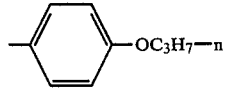 | H | H | n-C₃H₇ | n-C₃H₇ | H | m.p. 102°–106° C. |
| 74 | H | 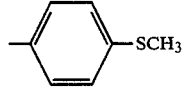 | H | H | CH₃ | CH₃ | H | m.p. 159°–161° C. |

TABLE 1-continued

| Compound No. | R¹ | R² | R³ | R⁴ | R⁵ | R⁶ | R⁷ | Physical property melting point or refractive-index |
|---|---|---|---|---|---|---|---|---|
| 75 | H | 4-(benzyloxy)phenyl | H | H | CH₃ | CH₃ | H | m.p. 172°–174° C. |
| 76 | H | 4-(benzyloxy)-3-methoxyphenyl | H | H | CH₃ | CH₃ | H | m.p. 71°–73° C. |
| 77 | H | 4-[(4-methoxybenzyl)oxy]phenyl | H | H | CH₃ | CH₃ | H | m.p. 202°–205° C. |
| 78 | H | 4-methylphenyl | H | H | H | H | CH₃ | m.p. 155°–160° C. |
| 79 | H | 2-furyl | H | H | CH₃ | CH₃ | H | m.p. 145° C. |
| 80 | H | cyclohexyl | H | H | CH₃ | CH₃ | H | m.p. 154° C. |
| 81 | H | cyclohexyl | H | H | C₂H₅ | C₂H₅ | H | m.p. 137°–139° C. |
| 82 | H | 2-thienyl | H | H | CH₃ | CH₃ | H | m.p. 165°–166° C. |
| 83 | H | 2-thienyl | H | H | C₂H₅ | C₂H₅ | H | m.p. 149°–152° C. |
| 84 | H | 1-naphthyl | H | H | CH₃ | CH₃ | H | m.p. 144°–148° C. |
| 85 | H | COOC₂H₅ | H | H | CH₃ | CH₃ | H | m.p. 155°–160° C. |
| 86 | H | COOCH₃ | H | H | CH₃ | CH₃ | H | m.p. 149°–152° C. |
| 87 | H | COOCH₃ | H | CH₃ | CH₃ | CH₃ | H | m.p. 150°–164° C. (decomposed) |
| 88 | H | 4-methylphenyl | H | H | H | H | H | m.p. 165°–170° C. |
| 89 | H | 2-furyl | H | H | H | H | H | m.p 156°–165° C. (decomposed) |

TABLE 1-continued

| Compound No. | R¹ | R² | R³ | R⁴ | R⁵ | R⁶ | R⁷ | Physical property melting point or refractive-index |
|---|---|---|---|---|---|---|---|---|
| 90 | H | 2-furyl | H | CH₃ | CH₃ | CH₃ | H | m.p. 140°–156° C. (decomposed) |
| 91 | H | 2-furyl | H | CH₃ | H | H | H | m.p. 120°–130° C. |
| 92 | H | 4-OCH₃-phenyl | H | CH₃ | H | H | H | m.p. 134.5°–136° C. |
| 93 | H | 4-CH₃-phenyl | H | CH₃ | H | H | H | m.p 142°–148° C. |
| 94 | H | 4-Cl-phenyl | H | CH₃ | H | H | H | m.p. 135.5°–141.5° C. |
| 95 | H | 2-Cl-phenyl | H | H | H | H | CH₃ | m.p 125°–137° C. (decomposed) |
| 96 | H | 2-furyl | H | H | H | H | CH₃ | m.p. 138°–150° C. (decomposed) |
| 97 | H | 3-Cl-phenyl | H | CH₃ | CH₃ | CH₃ | H | m.p. 75°–90° C. |
| 98 | H | 4-OCH₃-phenyl | H | CH₃ | CH₃ | CH₃ | H | m.p. 145°–149° C. |
| 99 | H | 4-OCH₃-phenyl | H | H | H | H | CH₃ | m.p. 140°–151° C. (decomposed) |
| 100 | H | —CH₂CHSC₂H₅<br>            │<br>            CH₃ | H | H | CH₃ | CH₃ | H | paste |
| 101 | H | 4-F-phenyl | COOC₂H₅ | H | CH₃ | CH₃ | H | m.p. 151°–153° C. |

TABLE 1-continued

| Compound No. | R¹ | R² | R³ | R⁴ | R⁵ | R⁶ | R⁷ | Physical property melting point or refractive-index |
|---|---|---|---|---|---|---|---|---|
| 102 | H | –C₆H₄–CH₃ (p) | COOC₂H₅ | H | CH₃ | CH₃ | H | m.p. 122°–124° C. |
| 103 | H | –C₆H₄–OCH₃ (p) | COOC₂H₅ | H | CH₃ | CH₃ | H | m.p. 106°–108° C. |
| 104 | H | –C₆H₄–Cl (o) | COOC₂H₅ | H | CH₃ | CH₃ | H | m.p. 117°–118° C. |
| 105 | H | 2-thienyl | H | CH₃ | CH₃ | CH₃ | H | m.p. 160°–164° C. |
| 106 | CH₃ | CH₃ | H | CH₃ | –CH₂CH=CH₂ | –CH₂CH=CH₂ | H | m.p. 101°–104° C. |
| 107 | CH₃ | CH₃ | H | H | C₂H₅ | C₂H₅ | H | m.p. 138°–140° C. |
| 108 | H | 2-furyl | H | H | H | CH₃ | H | m.p. 133°–137° C. |
| 109 | H | 2-thienyl | H | H | H | CH₃ | H | m.p. 113°–116° C. |
| 110 | H | H | H | CH₃ | H | H | H | m.p. 118°–130° C. |
| 111 | CH₃ | CH₃ | H | CH₃ | H | H | H | m.p. 130°–133° C. |
| 112 | H | t-C₄H₉ | COOC₂H₅ | H | CH₃ | CH₃ | H | m.p. 166° C. |
| 113 | H | phenyl | COOC₂H₅ | H | CH₃ | CH₃ | H | m.p. 102°–103° C. |
| 114 | H | phenyl | COOC₂H₅ | H | n-C₃H₇ | n-C₃H₇ | H | m.p. 185°–186° C. |
| 115 | H | –C₆H₄–OC₂H₅ (p) | COOC₂H₅ | H | CH₃ | CH₃ | H | m.p. 121°–123° C. |
| 116 | H | 2-furyl | COOC₂H₅ | H | CH₃ | CH₃ | H | m.p. 78°–81° C. |
| 117 | H | 2-thienyl | COOC₂H₅ | H | CH₃ | CH₃ | H | m.p. 97°–98° C. |
| 118 | CH₃ | CH₃ | H | H | H | CH₃ | H | m.p. 162°–164° C. 2 × hydrochloric acid salt |

TABLE 1-continued

| Compound No. | R¹ | R² | R³ | R⁴ | R⁵ | R⁶ | R⁷ | Physical property melting point or refractive-index |
|---|---|---|---|---|---|---|---|---|
| 119 | CH₃ | CH₃ | H | H | H | CH₃ | H | m.p 158°–163° C. 2 × hydrochloric acid salt |
| 120 | CH₃ | CH₃ | H | H | allyl | allyl | H | m.p. 160°–180° C. (decomposed) 2 × hydrochloric acid salt |
| 121 | H | 2-chlorophenyl | H | H | H | CH₃ | H | m.p. 151°–154° C. 2 × hydrochloric acid salt |
| 122 | H | 4-methoxyphenyl | H | H | CH₃ | CH₃ | H | m.p. 165°–190° C. (decomposed) 2 × hydrochloric acid salt |

The respective melting point of the compound numbers 118–122 in Table 1 shows the value of hydrochloric acid salt of said compounds.

Next, NMR spectra data of compound No. 100 is shown below.

NMR data (60 MHz, CDCl₃, δvalue) 1.12(3H, t, J=7.0 Hz), 1.24(3H, d, J=7.0 Hz) 1.20–1.70(3H), 2.40(6H, S), 2.0–3.10(11H) 4 35(2H, S)

Cyclohexanedione derivatives represented by the general formula (I) and their salts caused no toxic symptom nor death in mice or rats even after administrated continually for two weeks at a does of 300 mg/kg/day to the mice or rats, which reveals the markedly low toxicity of the compound of this invention. For example, LD₅₀ value (acute oral toxicity to male rat) of the compound No. 55 is more than 1,000 mg/kg.

The compounds represented by the general formula (I) and their salts are useful as a medicinal agent for treating liver diseases. For example, while it is known that hepatic disorders can be experimentally produced in healthy test animals by administering various agents such as carbon tetrachloride to the animals, as disclosed for example in U.S. Pat. No. 4,118,506, it has been found that the compounds represented by the general formula (I) and their salts give a marked effect of suppressing the lowering of liver functions when administered orally or parenterally (for example by injection) to test animals which have hepatic disorders of various pathologic models experimentally produced therein. Accordingly, the compounds represented by the general formula (I) and their salts are useful as a medicinal agent for curing or preventing hepatic disorders in men and animals. Thus, it can be used as a curative for acute or chronic hepatic disorders of men and animals produced by various causes, for example, jecure adiposum, alcoholic hepatitis, hepatitis, toxic liver disorders, cardiac cirrhosis, cholestatic liver disorder, or hepatocirrhosis which is the final state of these diseases.

Accordingly, the term "a pharmaceutical composition for treating hepatic disorders" as used in this invention means a medicinal agent for curing and/or preventing various disorders in liver by utilizing the pharmacological actions manifested in liver as mentioned above including the action of activating liver functions and the action of preventing and curing hepatic disorders.

The compound represented by the general formula (I) or its salt can be used as a medicinal agent for treating hepatic disorders in the form as it is; it may also be formulated, according to conventional pharmaceutical procedures, as a mixture thereof with a pharmaceutically acceptable diluents and/or other pharmacologically active substances. Further, it may be formulated into a dose unit form. Examples of the form which the compound can take as a medicinal agent include: powders, granules, tablets, dragée, capsules, pills, suspensions, solutions, liquid, emulsions, ampules, injections, and isotonic solutions.

The modes of preparing the compound of this invention into a pharmaceutical composition include one wherein the compound represented by the general formula (I) or its salt is contained as a mixture thereof with one or more pharmaceutically acceptable diluents.

The "diluent" referred to herein means a material other than the compound represented by the general formula (I) and their salts. It may be in the form of solid, semisolid, liquid, or ingestible capsules. Examples of the diluents include excipients, fillers, binders, moistening agents, disintegrators, surfactants, lubricants, dispersants, buffering agents, flavoring agents, odor correctives, coloring agents, flavors, preservatives, solubilizing aids, solvents, coating agents, and sugar-coating agents. However, they are not limited to these. Further, they may be used as a mixture of one or more kinds thereof. Sometimes, these pharmaceutically acceptable diluents are used as a mixture thereof with other pharmacologically active substances.

The pharmaceutical composition according to this invention may be prepared by any method known in the art. For instance, the active ingredient is mixed with a diluent and made up, for example, into granules. The resulting composition is then formed, for example, into tablets. Preparations to be administered parenterally should be made aseptic. Further, as occasion demands, they should be made isotonic with blood.

In this invention, since the compound represented by the general formula (I) and their salts mentioned above can be itself make a medicinal agent for treating liver diseases, the active ingredient is generally contained in the composition in a proportion of 0.01 to 100% by weight.

When the compound is made into a preparation in the form of dose unit, the individual parts of the preparation which form said preparation may be either in the same shape or in shapes different from each other. For example, the following shapes are often adopted: tablets, granules, pills, powders, dragée, capsules, ampules, and the like.

The medicinal agent for treating hepatic disorders according to this invention can be applied to men and animals for the purpose of preventing and treating hepatic disorders therein, in a manner conventional in the art. It is administered orally or parenterally. Oral administration referred to herein includes sublingual administration. Parenteral administration includes herein administrations conducted by means of injections (including, for example, subcutaneous, intramuscular or intravenous injection and instillation).

The dose of the medicinal agent of this invention varies depending upon various factors including whether it is applied to animals or men, difference in susceptibility, age, sex, body weight, the method, time, and interval of administration, the condition of diseases, physical condition, the properties of the pharmaceutical composition, the kind of the preparation, and the kind of the active ingredient.

Accordingly, sometimes those doses may be sufficient which are lower than the minimum of the dose range shown below, whereas sometimes it becomes necessary to administer an amount exceeding the upper limit of the dose shown below.

When the pharmaceutical composition is to be administered in a large amount, it is preferably administered divided in several doses per day.

In order to obtain effective results in application to animals, the agent is advantageously administered at a dose, in terms of the active ingredient, in the range of 0.1 to 500 mg, preferably 0.1 to 30 mg, per 1 kg of body weight per day in oral administration, and 0.01 to 250 mg, preferably 0.1 to 25 mg, per 1 kg of body weight per day in the case of parenteral administration.

The doses necessary for obtaining effective results in application to men are, judged from the effective doses in animals and in consideration of difference in susceptibility and safety, advantageously selected, for example, from the following dose range. In oral administration the dose is 0.1 to 200 mg, preferably 0.5 to 50 mg, per kg of body weight per day, and in parenteral administration it is 0.01 to 100 mg, preferably 0.1 to 25 mg, per kg of body weight per day.

EXAMPLE

This invention will be described in detail with reference to Examples, but it is in no way limited thereto.

First, synthesis examples of this invention are

EXAMPLE 1

[2-dimethyl-2,5-diaza-7,9-dithiabicyclo-(4,3,0)-nonane-8-ylidene]-5,5-dimethyl-1,3-cyclohexanedione. (compound No. 5)

To a suspension of 5.75 g (0.02 mole) of glyoxalsodium bisulfite in 20 ml of water was added dropwise with ice-cooling 1.5 g (0.02 mole) of N-methylethylenediamine. Then to this solution was added dropwise 1.92 g (0.02 mole) of N,N'-dimethylethylenediamine with ice-cooling and the mixture was stirred until it became a homogeneous solution. Then to this solution was added with ice-cooling the dithiolate solution prepared in the manner shown below; To mixture of 2.24 g (0.02 mole) of cyclohexanedione and 1.6 g (0.021 mole) of carbon disulfide in 15 ml of dimethylsulfoxide was added with ice-cooling 2.8 g (0.05 mole) of powdered potassium hydroxide and the mixture was stirred for 1 hour. dimedone and 1.6 g (0.021 mole) of carbon disulfide in 15 ml of dimethylsulfoxide was added with ice-cooling 2.8 (0.05 mole) of powdered potassium hydroxide and the mixture was stirred for 1 hour.

The reaction mixture was stirred, for additional 30 minutes and the crystalline precipitated was collected by filtration. This crystalline was washed with water, isopropylalcohol and hexane, and then recrystalized from isopropylalcohol to give 3.0 g of the desired product. Yield 50%; m.p. 158°–159° C.

EXAMPLE 2

2-[2-methyl-2,5-diaza-7,9-dithiabicyclo-(4,3,0)-nonane-8-ylidene]-5,5-dimethyl-1,3-cyclohexanedione. (compound No. 5).

To a suspension of 5.68 g (0.02 mole) of glyoxalsodium bisulfite in 30 ml of water was added dropwise with ice-cooling 1.5 g (0.02 mole) of N-methylethylenediamine. Then to this solution was added dropwise with ice-cooling the dithiolate solution prepared in the manner shown below; To mixture of 2.8 g (0.02 mole) of dimedone and 1.6 g (0.021 mole) of carbon disulfide in 20 ml of dimethylsulfoxide was added at room temperature 2.7 g (0.044 mole) of powdered potassium hydroxide and the mixture was stirred for 1 hour.

The reaction mixture was stirred for additional one hour at room temperature. The crystalline precipitated was collected by filtration and washed with water and hexane and recrystalized from chloroform-ether to give 1.5 g of the desired product.

Yield 24%; m.p. 156°–157° C.

EXAMPLE 3

2-[2,5-dimethyl-2,5-diaza-7,9-dithiabicyclo(4,3,0)-nonane-8-ylidene]-5-phenyl-1,3-cyclohexanedione. (compound No. 26)

To a suspension of 3.4 g (0.01 mole) of glyoxalsodium bisulfite in 20 ml of water was added dropwise at ° C. N,N'-dimethylethylenediamine and the mixture was stirred for 1 hour.

Then to this solution was added at 0° C. the dithiolate solution prepared in the manner shown below; To a solution of 1.9 g (0.01 mole) of 5-phenyl-1,3-cyclohexanedione and 0.9 g (0.012 mole) of carbon disulfide in 10 ml of dimethylsulfoxide was added at 10° C. 1.5 g of powdered potassium hydroxide and stirred for 1 hour.

After the completion of addition, the mixture was stirred for 1 hour. The solid precipitated was collected by filtration and washed with water and then recrystalized ethyl acetate-hexane to give 2.0 g of desired product.

Yield 53%; m.p. 149°–153° C.

EXAMPLE 4

2-[2,5-di-n-butyl-2,5-diaza-7,9-dithiabicyclo-(4,3,0)-nonane-8-ylidene]-5-phenyl-1,3-cyclohexanedione. (Compound No. 29)

The mixture of 3.4 g (0.01 mole) of glyoxalsodium bisulfite and 3.0 g (0.018 mole) of N,N'-di-n-butylethylenediamine in 30 ml of water was stirred for 1 hour at 0° C. Then to this solution was added dropwise at 0° C. the dithiolate solution prepared by the reaction of 1.9 g (0.01 mole) of 5-phenylcyclohexane-1,3-dione with 0.9 g (0.012 mole) of carbon disulfide in 10 ml of dimethylsulfoxide in the presence of 1.5 g (0.027 mole) of powdered potassium hydroxide.

The reaction mixture was stirred for 2 hours. Then 50 ml of water was added to the reaction solution. The crystalline precipitated was collected by filtration, washed with water and dried up and then recrystalized from ethyl acetate-n-hexane to give 1.7 g of the desired product.

Yield 37%; m.p. 130°–132° C.

EXAMPLE 5

2-[2,5-diaza-7,9-dithiabicyclo-(4.3.0)-nonane8-ylidene-5-(4-methoxyphenyl)-1,3-cyclohexanedione. (Compound No. 53)

To a suspension of 5.68 g (0.02 mole) of glyoxalsodium bisulfite in 30 ml of water was added dropwise at room temperature 1.44 g (0.024 mole) of ethylenediamine and the mixture was stirred until it became a homogeneous solution.

Then to this solution was added with ice-cooling the dithiolate solution prepared in the manner shown below; To a solution of 4.09 g (0.02 mole) of 5-(4-methoxyphenyl)-1,3-cyclohexanedione and 1.6 g (0.021 mole) of carbon disulfide in 20 ml of dimethylsulfoxide was added 2.8 g (0.05 mole) of powdered potassium hydroxide, and the mixture was stirred for one hour. The reaction mixture was stirred for additional minutes at 0° C. The crystalline precipitated was collected by filtration, washed with water, and dried and recrystalized from chloroform-ether to give 1.45 g of the desired product.

Yield 20%; m.p. 160–162° C.

EXAMPLE 6

2-[2,5-dimethyl-2,5-diaza-7,9-dithiabicyclo-(4.3.0)-nonane-8-ylidene]-5-(2-thienyl)-1,3-cyclo hexanedione. (compound No. 82)

To a suspension of 2.84 g (0.01 mole) of glyoxalsodium bisulfite in 20 ml of water was added dropwise at room temperature 1.05 g (0.01 mole) of N,N'-dimethylethylenediamine and the mixture was stirred until it became a homogeneous solution. Then to this solution was added with ice-cooling the dithiolate solution prepared in the manner mentioned below; To a solution of 1.94 g (0.01 mole) of 5-thienyl-1,3-cyclohexanedione and 0.8 g (0.01 mole) of carbon disulfide in 10 ml of dimethylformamide was added with ice-cooling 1.4 g (0.025 mole) of powdered potassium hydroxide, and the mixture was stirred for one hour.

The reaction mixture was stirred for additional 30 minutes. The crystalline precipitated was collected by filtration, washed with water, dried and then recrystalized from chloroform-ether to give 1.07 g of the desired product.

Yield 28%; m.p. 165°–166° C.

EXAMPLE 7

2-[1,2,5-trimethyl-2,5-diaza-7,9-dithiabicyclo(4.3.0)-nonane-8-ylidene]-5,5-dimethyl-1,3-cyclohexanedione. (compound No. 12)

To a solution of 4.58 g (0.04 mole) of sodium bisulfite was added 3.96 g (0.02 mole) of 40% methylglyoxal and the mixture was stirred for 1 hour at room temperature.

To this solution was added dropwise with ice-cooling 1.94 g (0.022 mole) of N,N'-dimethylethylenediamine and the mixture was stirred for 1 hour. Then to this solution was added with ice-cooling the dithiolate solution prepared in the manner shown below; To a mixture of 2.8 g (0.02 mole) of dimedone and 1.6 g (0.02 mole) of carbon disulfide in 15 ml of dimethylsulfoxide was added 2.7 g (0.044 mole) of powdered potassium hydroxide, and the mixture was stirred for one hour.

The reaction solution was stirred for additional 20 minutes and the solid precipitated was collected by filtration. The solid was dissolved in chloroform, and the solution was washed with water and dried over anhydrous sodium sulfate. After chloroform was evaporated in vacuo, the residue was recrystalized from chloroform-ether to give 0.55 g of the desired product.

Yield 8%; m.p. 161°–162° C.

EXAMPLE 8

2-[3-methyl-2,5-diaza-7,9-dithiabicyclo-(4.3.0) nonane-8-ylidene]-5,5-dimethyl-1,3-cyclohexanedione. (compound No. 14)

To a suspension of 5.68 g (0.02 mole) of glyoxalsodium bisulfite in 20 ml of water was added dropwise with ice-cooling 1.49 g (0.02 mole) of 1,2-propanediamine and the mixture was stirred until it became a homogeneous solution. Then to this solution was added with ice-cooling the dithiolate solution prepared in the manner shown below; To a solution of 2.8 g (0.02 mole) of dimedone and 1.6 g (0.02 mole) of carbon disulfide in 20 ml of dimethylsulfoxide was added with ice-cooling 2.7 g (0.044 mole) of powdered potassium hydroxide, and the mixture was stirred for one hour.

The reaction mixture was extracted with ethyl acetate, washed three times with ice-water and dried over anhydrous magnesium sulfate. The solvent was evaporated and the residue was recrystalized from ethyl acetate-hexane to give 0.8 g of the desired product.

Yield 13%; m.p. 150.0° C.

EXAMPLE 9

2-[2,5-acetyl-3-methyl-2,5-diaza-7,9-dithiabicyclo-(4.3.0)-nonane-8-ylidene]-5,5-dimethyl-3-cyclohexanedione in 5 ml of 1,3-cyclohexanedione. (compound No. 15)

To a solution of 0.4 g (0.0013 mole) of 2-[3-methyl-2,5-diaza-7,9-dithiabicyclo-(4.3.0)-nonane-8-ylidene]-5,5-dimethyl-1,3-cyclohexanedione in 5 ml of pyridine was added dropwise with ice-cooling 0.79 g (0.01 mole) of acetyl chloride and the mixture was stirred for 1 hour.

The reaction solution was extracted with ethyl acetate, washed with 2 N hydrochloric acid and water, and then dried over magnesium sulfate. The solvent was removed and the residue was washed with ether and recrystalized from ethyl acetate-hexane to give 0.35 g of the desired product.

Yield 68%; m.p. 146°–150° C.

EXAMPLE 10

2-[2-methyl-2,5-diaza-7,9-dithiabicyclo-(4,3,0)-nonane-8-ylidene]-5,5-dimethyl-1,3-cyclohexanedione dihydrochloride salt. (compound 118)

Into a solution of 1.0 g (0.0032 mole) of 2-[2-methyl-2,5-diaza-7,9-dithiabicyclo-(4.3.0)-nonane-8-yliden]-5,5-dimethyl-1,3-cyclohexanedione i 20 ml of acetone was bubbled dry hydrogen chloride with ice-cooling. After the crystalline was precipitated, to this solution was added 20 ml of ether to crystalize further the product dissolved in acetone.

The crystalline was collected by filtration and was washed with ether to give 1.1 g of the desired product.

Yield 90%; m.p. 162°–164° C.

Now, Examples regarding pharmaceutical compositions according to this invention will be described below. In the Examples, "part" is all part by weight. It is needless to say that the kinds and the proportions of the compounding ingredients used in the composition according to this invention can be changed variously without being restricted by these Examples.

EXAMPLE 11

| Compound No. 4 | 10 parts |
|---|---|
| Heavy magnesium oxide | 10 parts |
| Lactone | 80 parts |

The above ingredients were mixed uniformly and made into a medicinal preparation in the form of powders or fine granules.

EXAMPLE 12

| Compound No. 43 | 10 parts |
|---|---|
| Synthetic aluminum silicate | 10 parts |
| Calcium hydrogen phosphate | 5 parts |
| Lactose | 75 parts |

The above ingredients were used to be made up into powders in a similar manner to that in Example 11.

EXAMPLE 13

| Compound No. 53 | 50 parts |
|---|---|
| Starch | 10 parts |
| Lactose | 15 parts |
| Crystalline cellulose | 20 parts |
| Polyvinyl alcohol | 5 parts |
| Water | 30 parts |

The above ingredients were uniformly mixed, kneaded, then crushed, granulated, dried and sieved to obtain granules.

EXAMPLE 14

A mixture of 99 parts of the granules obtained in Example 13 and 1 parts of calcium stearate was compression-formed into tablets of 10 mm diameter.

EXAMPLE 15

| Compound No. 79 | 78 parts |
|---|---|
| Polyvinyl alcohol | 2 parts |
| Lactose | 20 parts |
| Water | 30 parts |

The above ingredients were made up into granules in the same manner as in Example 13. Ten parts of crystalline cellulose was added to 90 parts of the granules obtained above, and the mixture was compression-molded to obtain tablets of 8 mm diameter. The tablets may be further made up into dragée by using, in appropriate amounts, a mixed suspension of syrup, gelatin a precipitated calcium carbonate, and a coloring agent.

EXAMPLE 16

| Compound No. 95 | 0.5 part |
|---|---|
| Nonionic surfactant | 2.5 parts |
| Physiological saline | 97 parts |

The above ingredients were mixed with warming, then sterilized to obtain injections.

EXAMPLE 17

The powders obtained in Example 11 were filled into capsule containers available on the market to obtain capsules.

The effect of the compound of the present invention will be illustrated by the following Test Example.

Test Example 1

Effect of suppressing hepatic disorder caused by carbon tetrachloride.

Test Method

The test compound was dissolved or suspended in olive oil, and orally administered at a dose of 30 mg/kg to mice (6 weeks of age, dd-strain, ♂) Six hours thereafter, carbon tetrachloride was orally administered in a proportion of 0.05 ml/kg. The animals were sacrificed 24 hours after the administration of carbon tetrachloride, and the extent of liver injury was examined.

On the other hand, blood was collected from the animal at the time of the sacrifice, and centrifuged to obtain plasma. The plasma glutamic pyruvic transminase (GPT) activity was determined according to the method of Reitman-Frankel. The activity was expressed in terms of Karmen Units (K.U.). The conditions of the liver were expressed in terms of liver injury index as follows.

| Liver injury index | Condition of liver |
|---|---|
| 0 | Healthy liver |
| 2 | Slightly affected |
| 4 | Evidently observed injury |
| 6 | Serious injury |

Mice were used in groups of five of test were represented by the mean value. When the GPT activity was 2,000 units or higher, or further determination was made, the activity was calculated as 2,000 units for reasons of convenience.

The results obtained are shown in Table 2.

TABLE 2

| | Effect of carbon tetrachloride on liver injury | |
|---|---|---|
| No. of compound of this invention | Liver injury index | P-GPT (K.U.) |
| Administration of carbon tetrachloride alone | 6.0 | 2000 |
| No treatment | 0 | 12 |
| 1 | 0.2 | 14 |
| 2 | 0.4 | 15 |
| 4 | 0 | 11 |
| 6 | 0 | 19 |
| 7 | 0 | 16 |
| 10 | 0 | 41 |
| 11 | 0.5 | 16 |
| 12 | 0.4 | 33 |
| 14 | 0.4 | 18 |
| 18 | 1.2 | 22 |
| 21 | 0.1 | 23 |
| 25 | 0.8 | 15 |
| 26 | 0 | 12 |
| 28 | 0.2 | 39 |
| 32 | 0.3 | 22 |
| 36 | 1.5 | 268 |
| 41 | 0.4 | 213 |
| 42 | 0 | 14 |
| 43 | 0.2 | 24 |
| 47 | 0 | 24 |
| 48 | 0.3 | 18 |
| 51 | 0 | 81 |
| 52 | 0.1 | 14 |
| 53 | 0.1 | 13 |
| 55 | 0.3 | 107 |
| 56 | 2.5 | 50 |
| 57 | 0.2 | 142 |
| 59 | 0.1 | 16 |
| 60 | 0.1 | 26 |
| 61 | 1.5 | 494 |
| 63 | 0 | 15 |
| 65 | 1.6 | 347 |
| 78 | 0.2 | 18 |
| 79 | 0 | 30 |
| 80 | 1.0 | 405 |
| 82 | 0.3 | 16 |
| 90 | 0 | 15 |
| 92 | 0.4 | 15 |
| 102 | 1.5 | 319 |
| 103 | 1.0 | 18 |
| 104 | 1.7 | 345 |
| 105 | 0 | 15 |
| 106 | 1.2 | 242 |
| 108 | 1.0 | 24 |
| 109 | 0 | 17 |
| 111 | 1.0 | 14 |
| 114 | 2.2 | 26 |
| 115 | 0 | 39 |
| 118 | 0 | 32 |
| 119 | 0 | 15 |
| 121 | 0 | 20 |
| 122 | 1.5 | 231 |

What is claimed is:

1. A cyclohexanedione derivative represented by the formula (I):

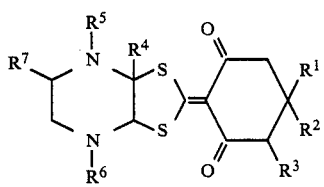

wherein $R^1$, $R^4$, and $R^7$ represent independently hydrogen atom or $C_1$-$C_8$ alkyl, $R^2$ represents hydrogen atom; $C_1$-$C_8$ alkyl; $C_2$-$C_6$ alkenyl; $C_3$-$C_8$ cycloalkyl; $C_2$-$C_7$ alkoxycarbonyl; $C_1$-$C_6$ alkylthio; $C_1$-$C_6$ alkyl; a phenyl; a phenyl group substituted with 1 to 3 groups selected from the group consisting of halogen atom, $C_1$-$C_6$ $C_6$ alkyl, $C_1$-$C_6$ haloalkyl, $C_1$-$C_6$ alkoxy, $C_1C_1$-$C_6$ alkylthio, $C_3$-$C_8$ cycloalkoxy, a benzyloxy and a benzyloxy group substituted with $C_1$-$C_6$ alkoxy; naphthyl, furyl or thienyl, $R^3$ represents hydrogen atom, $C_1$-$C_8$ alkyl or $C_2$-$C_7$ alkoxycarbonyl, and $R^5$ and $R^6$, which may be the same or different, represent hydrogen atom, $C_1$-$C_6$ alkyl, $C_2$-$C_6$ alkenyl, $C_2$-$C_7$ alkylcarbonyl or $C_2$-$C_7$ haloalkylcarbonyl or its pharmaceutically acceptable salts.

2. A cyclohexanedione derivative or its pharmaceutically acceptable salts according to claim 1, wherein $R^1$, $R^3$, $R^4$, and $R^7$, which may represents independently hydrogen atom or a lower alkyl, $R^2$ represents hydrogen atom; a lower alkyl; an alkenyl; a cycloalkyl; a phenyl; a phenyl group substituted with 1 to 3 groups selected from the group consisting of halogen atom, a lower alkyl, a lower haloalkyl, a lower alkoxy, a cycloalkoxy, benzyloxy and benzyloxy group substituted with lower alkoxy; naphthyl, furyl or thienyl, and $R^5$ and $R^6$, which may be the same or different, represent hydrogen atom, a lower alkyl; a lower alkenyl, an alkylcarbonyl or a haloalkyl carbonyl.

3. A cyclohexanedione derivative or its pharmaceutically acceptable salts according to claim 1, wherein $R^1$, $R^3$, $R^4$, $R^5$, $R^6$ and $R^7$ represent independently hydrogen atom or $C_1$-$C_4$ alkyl, and $R^2$ represents hydrogen atom; $C_1$-$C_4$ alkyl; a phenyl; a phenyl group substituted with 1 to 2 groups selected from the group consisting of halogen atom, $C_1$-$C_4$ alkyl and $C_1$-$C_4$ alkoxy; or furyl.

4. A cyclohexanedione derivative as in any one of claims 1 to 3 which is 2-[2,5-dimethyl-2,5-diaza-7,9-dithiabicyclo-(4.3.0)-nonane-8-ylidene]-1,3-cyclohexanedione.

5. A cyclohexanedione derivative as in any one of claims 1 to 3 which is 2[2,5-dimethyl-2,5-diaza-7,9-dithiabicyclo-(4.3.0)-nonane-8-ylidene-5,5-dimethyl-1,3-cyclohexanedione.

6. A cyclohexanedione derivative as in any one of claims 1 to 3 which is 2-[2-methyl-2,5-diaza-7,9-dithiabicyclo-(4.3.0)-nonane-8-ylidene]-5-(2-chlorophenyl)-1,3-cyclohexanedione.

7. A cyclohexanedione derivative as in any one of claims 1 to 3 which is 2-[2,5-dimethyl-2,5-diaza-7g,9-dithiabicyclo-(4.3.0)-nonane-8-ylidene]-5-(4-tolyl)-1,3cyclohexanedione.

8. A cyclohexanedione derivative as in any one of claims 1 to 3 which is 2-[2,5-dimethyl-2,5-diaza-7,9-dithiabicyclo-(4.3.0)-nonane-8-ylidene]-5-(4-methoxyphenyl)1,3-cyclohexanedione.

9. A cyclohexandione derivative as in any one of claims 1 to 3 which is 2-[2,5-diaza-7,9-dithiabicyclo(4.3.0)-nonane-8-ylidene]-5-(4-methoxyphenyl)-1,3-cyclohexanediondione.

10. A cyclohexandione derivative as in any one of claims 1 to 3 which is 2-[2,5-dimethyl-2,5-diaza-7,9-dithiabicyclo-(4,3,0)-nonane-8-ylidene]-5-(2-furyl)-1,3-cyclohexanedione.

11. A cyclohexanedione derivative as in any one of claims 1 to 3 which is 2-[1,2,5-trimethyl-2,5-diaza-7g,9-dithiabicyclo-(4.3.0)-nonane-8-ylidene]-5-(2-furyl)-1,3-glygclohexandione.

12. A cyclohexanedione derivative as in any one of claims 1 to 3 which is 2-[methyl-2,5-diaza-7,9-dithiabicylo (4.3.0)-nonane-8-ylidene]-5-(4-methoxyphenyl)-1,3-cyclohexanedione.

13. A cyclohexanedione derivative as in any one of claims 1 to 3 which is 2-[3-methyl-2,5-diaza-7,9-dithiabicyclo(4.3.0)-nanone-8-ylidene]-5-(4-methoxyphenyl)-1,3cyclohexanedione.

14. A pharmaceutical composition for treating hepatic disorder, comprising an effective amount of a cyclohexanedione derivative represented by the formula (I):

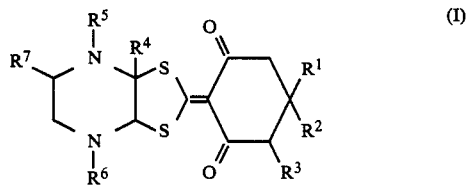

wherein $R^1$, $R^4$ and $R^7$ represent independently hydrogen atom or $C_1$–$C_8$ alkyl, $R^2$ represents hydrogen atom; $C_1$–$C_8$ alkyl; $C_2$–$C_6$ alkenyl; $C_3$–$C_8$ cycloalkyl; $C_2$ $C_7$ alkoxycarbonly; $C_1$–$C_6$ alkylthio $C_1$–$C_8$ alkyl; a phenyl; a phenyl group substituted with 1 to 3 groups selected form the group consisting of halogen atom, $C_1$–$C_8$ alkoxy, $C_1$–$C_6$ alkylthio, $C_3$–$C_8$ cyloalkoxy, a benzyloxy and a benzyloxy group substituted with $C_1$–$C_6$ alkoxy; naphthyl, furyl or thienyl, $R^3$ represents hydrogen atom, $C_1$–$C_8$ alkyl or $C_2$–$C_7$ alkoxy-carbonyl, and $R^5$ and $R^6$, which may be the same or different, represent hydrogen atom, $C_1$–$C_6$ alkyl, $C_2$–$C_6$ alkenyl, $C_2$–$C_7$ alkylcarbonyl or $C_2$–$C_7$ haloalkylcarbonyl, or its pharmaceutically acceptable salts, and a pharmaceutical carrier.

15. A pharmaceutical composition according to claim 14, wherein $R^1$, $R^3$, $R^4$ and $R^7$ represent independently hydrogen atom or a lower alkyl, $R^2$ represents hydrogen atom; a lower alkyl; an alkenyl; a cycloalkyl; a phenyl; a phenyl group substituted with 1 to 3 groups selected from the group consisting of halogen atom, a lower alkyl, a lower haloalkyl, a lower alkoxy, a cycloalkoxy, a benzyloxy and a benzyloxy group substituted with lower alkoxy; naphthyl, furyl or thienyl, and $R^5$ and $R^6$, which may be the same or different, represent hydrogen atom, a lower alkyl, a lower alkenyl, an alkylcarbonyl or a haloalkyl carbonyl.

16. A pharmaceutical composition according to claim 14, wherein $R^1$, $R^3$g, $R^4$, $R^5$, $R^6$ and $R^7$ represent independent hydrogen atom or $C_1$–$C_4$ alkyl and $R^2$ represents hydrogen atom; $C_1$–$C_4$ alkyl; a phenyl; a phenyl group substituted with 1 to 2 groups selected from the group consisting of halogen atom, $C_1$–$C_4$ alkyl and $C_1$–$C_4$ alkoxy; or furyl.

17. A pharmaceutical composition as in any one of claims 14 to 16, in which said cyclohexanedione derivative is 2-[2,5-dimethyl-2,5-diaza-7,9-dithiabicyclo-(4.3.0)-nonane-8-ylidene-1,3-cyclohexanedione.

18. A pharmaceutical composition as in any one of claims 14 to 16, in which said cyclohexanedione derivative is 2-[2,5-dimethyl-2,5-diaza-7,9-dithiabicyclo-(4.3.0)-nonane-8-ylidene]-5,5-dimethyl-1,3-cyclohexanedione.

19. A pharmaceutical composition as in any one of claims 14 to 16, in which said cyclohexanedione derivative is 2-[2,5-methyl-2,5-diaza-7,9-dithiabicyclo-(4.3.0)-nonane-8-ylidene]-5-(2-chlorophenyl)-1,3-cyclohexanedione.

20. A pharmaceutical composition as in any one of claims 14 to 16, in which said cyclohexanedione derivative is 2-[2,5-dimethyl-2,5-diaza-7,9-dithiabicyclo-(4.3.0)-nonane-8-ylidene]-5-(4-tolyl)-1,3-cyclohexanedione.

21. A pharmaceutical composition as in any one of claims 14 to 16, in which said cyclohexanedione derivative is 2-[2,5-dimethyl-2,5-diaza-7,9-dithiabicyolo-(4.3.0)-nonane-8-ylidene]-5-(4-methoxyphenyl)-1,3-cyclohexanedione.

22. A pharmaceutical composition as in any one of claims 14 to 16, in which said cyclohexanedione derivative is 2-[2,5-diaza-7,9-dithiabicyclo-(4.3.0)-nonane-8-ylidene]-5-(4-methoxyphenyl)-1,3-cyclohexanedione.

23. A pharmaceutical composition as in any one of claims 14 to 16, in which said cyclohexanedione derivative is 2-[2,5-dimethyl-2,5-diaza-7,9-dithiabicyclo-(4.3.0)-nonane-8-ylidene]-5-(4-tolyl)-1,3-cyclohexanedione.

24. A pharmaceutical composition as in any one of claims 14 to 16, in which said cyclohexanedione derivative is 2-[1,2,5-trimethyl-2,5-diaza-7,9-dithiabicyclo(4.3.0)-nonane-8-ylidene]-5-(2-furyl)-1,3-cyclohexanedione.

25. A pharmaceutical composition as in any one of claims 14 to 16, in which said cyclohexanedione derivative is 2-[-methyl-2,5-diaza-7,9-dithiabicyclo-(4.3.0)-nonane8-ylidene]-5-(4-methoxyphenyl)-1,3-cyclohexanedione.

26. A pharmaceutical composition as in any one of claims 14 to 16, in which said cyclohexanedione derivative is 2-3-methyl-2,5-diaza-7,9-dithiabicyclo-(4.3.0)-nonane-8-ylidene-5-(4-methoxyphenyl)-1,3-cyclohexanedione.

* * * * *